US008283136B2

(12) United States Patent
Tagg et al.

(10) Patent No.: US 8,283,136 B2
(45) Date of Patent: Oct. 9, 2012

(54) SKIN TREATMENT COMPOSITIONS

(75) Inventors: John Robert Tagg, Dunedin (NZ); Christopher Norman Chilcott, Dunedin (NZ); Mohammed Abdullah Ali Alqumber, Dunedin (NZ)

(73) Assignee: Blis Technologies Limited, Dunedin (NZ)

( * ) Notice: Subject to any disclaimer, the term of this patent is extended or adjusted under 35 U.S.C. 154(b) by 0 days.

(21) Appl. No.: 12/710,542

(22) Filed: Feb. 23, 2010

(65) Prior Publication Data

US 2011/0189133 A1    Aug. 4, 2011

Related U.S. Application Data

(63) Continuation of application No. 12/504,403, filed on Jul. 16, 2009, now abandoned, which is a continuation of application No. 11/887,693, filed on Oct. 1, 2007, now abandoned.

(30) Foreign Application Priority Data

Mar. 29, 2005  (NZ) ......................................... 539076
Mar. 29, 2006  (WO) ................. PCT/NZ2006/000060

(51) Int. Cl.
  *C12P 21/06*  (2006.01)
  *C12Q 1/02*   (2006.01)
  *C07K 1/00*   (2006.01)
  *C12N 1/12*   (2006.01)
  *C12N 1/20*   (2006.01)

(52) U.S. Cl. ....... 435/69.1; 435/29; 435/253.1; 530/350

(58) Field of Classification Search ................ 435/29, 435/69.1, 253.1; 530/350
See application file for complete search history.

(56) References Cited

U.S. PATENT DOCUMENTS

| 4,719,109 A * | 1/1988 | Kirsch et al. ................. 424/117 |
| 2004/0057917 A1 * | 3/2004 | Wolf et al. ....................... 424/59 |
| 2008/0193393 A1 * | 8/2008 | Dayan ............................. 424/59 |
| 2008/0226708 A1 * | 9/2008 | Lin et al. ....................... 424/450 |

FOREIGN PATENT DOCUMENTS

| CA | 2106631 | 3/1994 |
| DE | 4231544 | 2/1994 |
| DE | 4231543 | 3/1994 |
| EP | 0750903 | 1/1997 |

OTHER PUBLICATIONS

Bibel, D J and Smiljanic R J, Inhibition of diptheroid esterase by *Micrococcus luteus*, Can. J. Microbiol (1977) vol. 23, No. 10 pp. 1319-1326.
Liebl, W, et al., Plasmid-borne macrolide resistance in *Micrococcus luteus*, Microbiology (2002) pp. 2479-2487.
Roth, R R and James, W D, Microbial Ecology of the Skin, Ann. Rev. Microbiol (1988) vol. 42, pp. 441-464.

* cited by examiner

*Primary Examiner* — Karen Cochrane Carlson
*Assistant Examiner* — Natalie Moss
(74) *Attorney, Agent, or Firm* — Frommer Lawrence & Haug LLP

(57) ABSTRACT

This invention relates to *Micrococcus luteus* containing compositions useful for controlling skin disorders in which bacteria are a causative component. The invention also provides for a new strain of *Micrococcus luteus* useful in these compositions.

13 Claims, No Drawings

SKIN TREATMENT COMPOSITIONS

FIELD OF THE INVENTION

This invention relates to *Micrococcus luteus* containing compositions useful for controlling skin disorders, more particularly, the invention relates to compositions intended for topical application to prevent or treat skin disorders in which bacteria are a causative component, for example, body odour, skin infections and acne. A new strain of *Micrococcus luteus* useful in these compositions is also provided.

BACKGROUND OF THE INVENTION

Skin disorders including malodour are often attributable to the action of microorganisms on the skin. A range of products including proteins, lipids, salts and acids are secreted by glands in the skin. While the fresh secretions are often odourless, microbial decomposition of the secreted products can result in offensive odours being produced.

Control of body odour is most commonly addressed through the use of antiperspirants or deodorants. Deodorants are generally designed to mask offensive odours or to prevent production of same. Antiperspirants are intended to prevent or control perspiration on the skin, and may also function as a deodorant.

Most deodorant or antiperspirant products make use of aluminium salts or zinc salts. These compounds can cause irritation, itching and burning on individuals with sensitive skin. There exists a health concern amongst various groups of consumers about the health effects of using aluminium or other metal salts particularly in deodorants. Studies such as Graves et al., 1990 Journal of Clinical Epidemiology vol. 43. 35-44 and P. D. Dabre., 2003 Journal of Applied Toxicology vol 23, Issue 2, 89-95 imply a link between aluminium and Alzheimer's, and aluminium and breast cancer. Accordingly, development of an aluminium or zinc free deodorant or antiperspirant product is desirable.

Skin infections may be caused by a range of bacteria including *Staphylococcus* species, (particularly *S. aureus*), *Propionibacterium acnes, Corynebacterium* sps, and *Streptococcus* species as well as aerobic diphtheroids. Examples of such infections are toe infections, impetigo, folliculitis, cellulitis, boils, carbuncles, mastitis, and acne. Treatment often involves topical or oral administration of antibiotics, antifungals and in some cases steroids. Antibiotics and antifungals can also kill off non-pathogenic beneficial microorganisms leading to reinfection. Moreover, microorganisms are becoming increasingly antibiotic resistant see for example Antibiotic Resistance; Stephen Gillespie ed; Humana Press, 1 Sep. 2000. Accordingly, there is a constant need for alternative forms of treatment.

The present invention is broadly directed to compositions and methods for controlling skin disorders using *Micrococcus luteus* strains, or at least provides the public with a useful choice.

SUMMARY OF THE INVENTION

In a first aspect, the invention provides a biologically pure culture of *M. luteus* strain Q24 on deposit at Deutsche Sammlung von Mikroorganisms Und Zellkulturen GmbH, Braunschweig, Germany, under accession number DSM 17172, or a culture having the identifying characteristics thereof.

The invention also provides a composition comprising *M. luteus* strain Q24 or a culture having the identifying characteristics thereof together with a diluent, carrier and/or excipient.

In a further aspect, the invention provides a composition comprising a strain of *M. luteus* effective to at least inhibit one or more bacteria selected from the group consisting of *Staphylococcus* species, *Propionibacterium* species, *Corynebacterium* species, and *Streptococcus* species, and aerobic diphtheroids.

In a further aspect, the invention provides a composition comprising a strain of *M. luteus* effective to at least inhibit growth of one or more bacteria selected from the group consisting of *Propionibacterium acnes, Staphylococcus aureus, Staphylococcus saprophyticus, Staphylococcus simulans, Corynebacterium diphtheriae, Corynebacterium ulcerans, Corynebacterium minutissium, Corynebacterium tenuis, Streptococcus pyogenes Streptococcus agalactiae*, and *Streptococcus dysgalactiae* together with a diluent, carrier and/or excipient.

In one embodiment, the *M. luteus* strain inhibits at least four of the group of bacteria above, preferably eight and more preferably all eleven. These bacteria are generally recognised as skin bacteria.

In one embodiment the *Staphylococcus aureus* is methicillin resistant.

Preferably the *M. luteus* is strain Q24.

Preferably the composition is formulated for topical administration.

Topically administrable forms include powders, emulsions, unguents, pastes, oils, gels, lotions, creams, suspensions, nasal sprays, roll ons, sticks or aerosol sprays, semi-solid and solid formulations.

In a further aspect, the invention provides a method for at least inhibiting the growth of bacteria sensitive to *M. luteus*, the method comprising contacting the sensitive bacteria with an inhibitory effective amount of an *M. luteus* strain or a composition of the invention.

The invention also provides a prophylactic or therapeutic method of treatment for skin disorders in an individual in need thereof. The method comprising administering to said individual an *M. luteus* strain, or a composition of the invention in an amount effective to at least inhibit growth of one or more bacteria causing the skin disorder, or in an amount to allow effective colonisation of the skin of the individual by the *M. luteus*.

In a further aspect, the invention provides a method of controlling the incidence and/or severity of a skin disorder, the method comprising introducing to the skin of the individual an amount of *M. luteus*, or composition of the invention, effective to control the incidence or severity of said skin disorder.

Skin disorders amenable to treatment according to the present invention include skin infections, such as impetigo, erysiphelas, folliculitis, acne, boils, carbuncles, cellulitis, pitted keratolysis, intertrigo, trichomycosis, mastitis, toe infections such as tinea, and body odour.

Bacteria responsible for skin disorders that may be controlled according to the present invention include *Propionibacterium* species, including *Propionibacterium acnes, Streptococci* species including *Streptococcus pyogenes, Streptococcus agalactiae*, and *Streptococcus dysgalactiae, Staphylococcus* species including *Staphylococcus simulans, Staphylococcus saprophyticus* and *Staphylococcus aureus, Corynebacterium* species including *Corynebacterium diphtheriae, Corynebacterium ulcerans, Corynebacterium tenuls* and *Corynebacterium minutissimum*. Included in this group are aerobic diphtheroids. This is a group of *Corynebacterium* commonly regarded as responsible at least in part for body odour.

Optionally, the existing population of skin microflora is reduced prior to, or simultaneously with treatment using a method of the invention.

The invention also relates to the use of *M. luteus*, or compositions of the invention in the methods discussed above. Particularly, to the use of *M. luteus* in the preparation of medicament for use in treating skin disorders as above including body odour, skin infections (particularly acne), and toe infections.

Although the invention is broadly as described above, it will be appreciated by those persons skilled in the art that it is not limited thereto but also includes embodiments of which the following description gives examples.

DETAILED DESCRIPTION OF THE INVENTION

As noted above, the present invention is directed in a first aspect to *M. luteus* strain Q24. This *M. luteus* strain was deposited by the assignee under the terms of the Budapest Treaty with Deutsche Sammlung von Mikroorganismen Und Zellkulturen GmbH, Braunschweig, Germany on 10 Mar. 2005, and assigned Accession No. 17172.

*M. luteus* is a gram positive spherical saprophytic bacterium. The organism is a natural inhabitant of the human skin, and can occasionally be found in the mucous membranes. It is considered non-pathogenic and can be spread through direct contact. It is common in the environment but survives for only a limited time in soil or water. The species is a non-spore forming, obligate aerobe that produces creamy white to yellow insoluble pigments. A full morphological description is provided in the accompanying examples. Also contemplated herein are *M. luteus* strains having the identifying characteristics of Q24 as set forth in the examples. These strains may be mutants which are natural products or artificially produced by manipulations such as chemical or UV mutagenesis, or genetic modification.

*M. luteus* Q24 and other *M. luteus* strains having the identifying characteristics thereof are useful for at least inhibiting the growth of bacteria such as *Propionibacterium* species including *Propionibacterium acnes; Staphylococcus* species including *Staphylococcus aureus* (all of 24 tested strains were sensitive including 20 that were methicillin resistant), *Staphylococcus saprophyticus*; and *Staphylococcus simulans; Corynebacterium* species including, *Corynebacterium diphtheriae, Corynebacterium ulcerans, Corynebacterium tenuis, Corynebacterium minutissimum, Streptococcus pyogenes, Streptococcus agalactiae* and *Streptococcus dysgalactiae*. Included in this group are aerobic diphtheroids. This is a group of *Corynebacterium* commonly regarded as being at least in part responsible for body odour.

Without wishing to be bound by theory, it is currently believed that *M. luteus* serves as an effector strain to replace bacteria involved in causing skin disorders. An effector strain is one which can compete successfully with the disorder-causing organism either via competitive action (eg for attachment sites; or inhibition by other metabolism-associated by-products; or a combination thereof).

The *M. luteus* of the invention exhibit broad spectrum antibacterial activity. The *M. luteus* are therefore useful as an antibacterial agent per se as well as therapeutically. The *M. luteus* are also useful as an antifungal agent per se. In this context, "therapeutic" includes prophylactic treatment. Therapeutic uses include the treatment or prevention of bacterial infections, particularly *Staphylococcus, Streptococcus, Propionibacterium*, and *Corynebacterium* infections. The *Micrococcus luteus* of the invention are particularly suitable for use against the bacteria *S. aureus, P. acnes, Corynebacterium minutissimum* and *S. pyogenes* Conditions amenable to treatment with the strains or compositions of the invention include skin infections (including acne), toe infections, and body odour.

Common skin disorders and the organisms which are at least in part causative of the disorder are as follows:

TABLE A

| Disorder | Bacteria |
| --- | --- |
| Impetigo | *Streptococcus pyogenes* and/or *Staphylococcus aureus* |
| Erysiphelas | *Streptococcus pyogenes* |
| Folliculitis | *Staphylococcus aureus* |
| Boils | *Staphylococcus aureus* |
| Carbuncles | *Staphylococcus aureus* |
| Acne | *Propionibacterium acnes* |
| Pitted Keratolysis | Coryneform bacteria/Aerobic diphtheroids |
| Intertrigo[1] | Overgrowth of resident and transient bacteria |
| Erythasma | *Corynebacterium minutissimum* |
| Trichomycosis | *Corynebacterium tenuis* |
| Toe web infection[2] | Coryneform bacteria/aerobic diphtheroids |
| Body odour | Aerobic diphtheroids |
| Tinea[3] | *Staphylococcus* species and *Streptococcus* species |
| Mastitis[4] | *Staphylococcus aureus, Streptococcus agalactiae, Streptococcus dysgalatiae* |

[1]Intertrigo is polymicrobial disorder like many skin diseases the infection often results from infection by normal commonsal organisms of the skin. Resident and transient bacteria most usually include *Staphylococcus* species, *Streptococcus* species *Propionibacteria* species, aerobic diphtheroids and some *Candida* species.
[2]Toe web infection A polymicrobial infection involving coryneform bacteria aerobic diphtheroids, *Brevibacterium* and Gram-negative rods
[3]Tinea is a polymicrobial infection usually involving dermatophyte fungi such as *Trichophyton, Epidermophyton* and *Microsporum*. Secondary bacterial infections are also commonly implicated in Tinea's. Causative organisms include *Staphylococcus* species, *Streptococcus* species, *Pseudomonas*, and *Corynebacterium minutissimum*. (See Gupta A K et., Dermatology Clinics vol 21; p 431-62, 2003 Treatments of Tinea pedis).
[4]Mastitis is also a polymicrobial infection. Key causative organisms include *Staphylococcus aureus, Streptococcus agalactiae, Streptococcus dysgalactiae, Escherischia coli*, and *Klebsiella pneumoniae*.

The term "skin disorders" as used herein is therefore to be broadly understood as encompassing bacterial diseases of the skin, and mucosa. caused at least in part by one or more bacteria of the genera *Staphylococcus, Streptococcus, Corynebacterium*, and *Propionibacterium* or by bacteria of the group aerobic diphtheroids.

Specific skin disorders herein are those caused at least in part by *S. saprophyticus, S. simulans, S. aureus, S. pyogenes, S. agalactiae, S. dysgalactiae, C. diphtheriae, C. ulcerans, C. minutissium, C. tenuis* and *P. acnes*.

For treatment of skin disorders, topical therapeutic formulations are particularly useful. The term "topical" refers to compositions suitable for application to skin or mucosal surfaces of the body, Mucosal surfaces include the nasal cavity.

A "therapeutic formulation" is a formulation appropriate for administration of an *M. luteus* strain to an individual in need of same, particularly an individual susceptible to skin disorders. In general, therapeutic formulations of the invention are composed of an *M. luteus* strain of the invention and an acceptable carrier, diluent and/or excipient.

An "acceptable carrier, diluent and/or excipient" means a vehicle for delivery of a *M. luteus* strain of the invention, to the individual, in which the vehicle is compatible with bacterial cell viability. Acceptable carriers suitable for use in the administration of viable *M. luteus* strains of the invention are well known to those skilled in the art. Suitable carriers are generally inert and can be either solid or liquid.

In one embodiment, the carrier is a pharmaceutically acceptable carrier. Pharmaceutically acceptable carriers suitable for use with the *M. luteus* strains herein include, but are not limited to buffered saline solutions (e.g., phosphate-buffered saline), pharmaceutically acceptable culture media (e.g. TSB), or other solutions which maintain the viability of the bacterium. Additionally, such pharmaceutically acceptable carriers may be non-aqueous solutions, suspensions, and emulsions. A variety of pharmaceutically acceptable carriers suitable for administration of viable or lyophilized bacteria are well known in the art (see, for example, *Remington's Pharmaceutical Sciences*, 18th ed., Gennaro, ed., 1990, Mack Publishing Co., Easton, Pa., incorporated herein by reference. Suitable solid carriers known in the art include, for example, magnesium carbonate; magnesium stearate; celluloses; talc; sugars such as fructose, sucrose, dextrose, trehalose, mannitol, lactose; starches; and flours; but are not limited thereto.

Oleaginous carriers suitable for use in the compositions of the invention include glycerol, mineral oils, essential oils, fats, fatty acids and esters thereof, glycerides, propylene glycol, lanolin, and derivatives, lecithin and derivatives, white petrolatum petroleum jelly, emulsions formed from oil(s) and water, and may be mixed to form liquids, gels, creams, emulsions, pastes, suspensions, semi-solids, solids or aerosols amongst others. Detergents and surfactants such as Tween 80 may also be added.

Currently preferred for use are oils and fats such as cocco butter, shea butter, grapeseed oil and chamomile oil.

Phase formulations including aqueous and oil phases with the *M. luteus* or composition of the invention in an oil phase are also feasible. In one embodiment the phase formulation is a two phase formulation with one oil and one aqueous phase.

The compositions may also include excipients such as known art preservatives; thickening agents; opacifiers; binders; antioxidants; emulsifiers; buffers; colourings; anti-caking agents; fillers; mineral salts; essential oils; botanical extracts; and fragrances as appropriate. Nutrients (for example carbohydrates such as xylitol, lactose and maltose or the like, and/or proteins such as casein) to maintain viability of *M. luteus* may also be included. Emollients to improve cosmetic properties and facilitate application of the composition can also be included. Examples of emollients are silicones such as DC246 and DC556 (Dow Corning, USA), fatty acid esters such as Esto/RTM1517 (Unichem) but are not limited thereto. The carriers and excipients selected must not significantly affect the antibacterial, activity of the *M. luteus*.

A currently preferred composition includes a salt such as rock salt or sodium chloride but not limited thereto. Because many bacteria and fungi involved in skin disorders are salt sensitive, the inclusion of salt in the composition also helps to reduce the bacterial populations on the skin. nails or mucosa. This allows for more effective colonisation by the *M. luteus* strain.

Salt is most usually included at a concentration of 1 to 10%, preferably 3 to 7%, and more preferably 5% by weight of the composition The *M. luteus* strains of the invention can be formulated in any of a variety of compositions suitable for topical administration, including mucosal administration. For example, the *M. luteus* strains can be formulated for administration as a lyophil or cell paste prepared from a *M. luteus* culture, or can be directly administered to the site of the skin disorder. The strain can also be administered in the form of a cream, gel, emulsion, oil, paste, lotion, wash, suspension, spray (including nasal spray), powder, stick, roll-on or aerosol, solid or semi-solid but the forms are not limited thereto.

For treatment of body odour, roll-on powder, aerosol or stick deodorant formulations are feasible. Currently preferred for use are stick formulations. All formulations can be readily produced according to known art techniques. For example a deodorant stick may be produced by melting cocco and shea butter, and mixing in freeze-dried *M. luteus* powder. The mixture is then poured into a deodorant stick container and cooled until solid.

For acne treatment the *M. luteus* can be a component of a face wash, soap, lotion, cream unguent gel, emulsion or the like. The *M. luteus* may conveniently form part of an existing skin treatment regime product. For example, a face wash, cleanser or moisturiser.

For skin infections including tinea the *M. luteus* can be formulated as a powder, oil, wash, cream, soap, ungent lotion, or spray (including nasal sprays).

Formulations such as bath oils, and soaps are useful for treating skin infections identified herein.

For general antimicrobial use, formulations may also be produced for other methods of administration including transdermal administrable formulations, but not limited thereto.

The *M. luteus*, compositions and formulations of the invention may also be topically administered indirectly, such as in material for contacting the skin or mucosa. For example, in nappies, wet wipes, sanitary pads, clothing articles and the like. The *M. luteus* can be applied to the material by known art techniques such as spraying and drying.

The formulations and compositions of the invention may further comprise one or more secondary antibacterial agents. These secondary agents may, for example, be antibiotics, or other antibacterial agents or antibacterial producing microorganisms. Useful antibacterials include bacteriocin-like inhibiting substances (BLIS) such as nisin, epidermin and salivaricins A, $A_1$, $A_2$ and B for example. Other antibacterial compounds such as potassium alum may also be included. Any antibacterial must also be compatible with *M. luteus* viability. The secondary antibacterial may be included at a concentration of 1 to 20%, commonly 3 to 15%, preferably 4 to 10%, more preferably 1 to 9%, by weight of the composition and even more preferably 7.5%.

The *M. luteus* comprise about 0.01% to about 99% by weight of the final composition, commonly 0.05 to 50%, preferably 0.075 to 20%, more preferably 0.1 to 10% by weight of the composition or formulation suitable for topical administration.

In the treatment of skin disorders, *M. luteus* strains of the invention can be administered to any susceptible individual.

The term "individual" as used herein includes humans, horses, dogs, cats, pigs, sheep, cattle, goats but is not limited thereto. Preferably, the individual is a human. The *M. luteus* strains can be administered to the individual at any age, e.g. childhood, adolescence, or adulthood.

The *M. luteus* of the invention can be administered in a variety of ways. For example, in the form of compositions or formulations discussed above, or as suspensions, sustained release formulae or lyophil powders. The *M. luteus* strains can also be administered by direct application of a lyophil, culture, or cell paste to the affected skin, nail or mucosal surface of the individual. Any mode of administration is suitable as long as the therapeutic formulation is applied to the skin, or mucosa.

In general, the amount of *M. luteus* administered to the individual will be an amount effective for replacement of skin disorder causing bacteria or fungi on the skin of the individual. "An amount effective for replacement of skin disorder causing bacteria on the skin of the individual means an amount effective for skin colonisation by the *M. luteus* strain, and significant reduction of the resident skin disorder-causing bacteria (e.g. by competition between the bacteria for attachment sites, nutrients and/or by antibacterial action).

The term "unit dose" when used in reference to a therapeutic formulation of the present invention refers to physically discrete units suitable as unitary dosage for the individual, each unit containing a predetermined quantity of active material (viable *M. luteus*) calculated to produce the desired therapeutic effect in association with the required diluent, carrier, or excipient.

Specific dosages can vary widely according to various individual variables including size, weight, age, disease severity (e.g. the tenacity and/or number of skin disorder causing resident bacteria, or fungi) and responsiveness to therapy (e.g. the susceptibility of the individual's skin to colonisation). Methods for determining the appropriate route of administration and dosage may be determined by the consumer as they deem appropriate, or on a case-by-case basis by an attending doctor, pharmacist, or other clinician. Such determinations are routine to one of ordinary skill in the art (see for example, *Remington's Pharmaceutical Sciences*, 8th ed., Gennaro, ed., Mack Publishing Company, Easton, Pa., 1990).

In general, the number of *M. luteus* administered to the individual will range from about $10^2$ to $10^{15}$ bacteria, preferably from about $10^3$ to $10^{10}$ bacteria, more preferably from about $10^4$ to $10^8$ bacteria, normally about $10^6$ to $10^7$ colony forming units (CFU) per dose.

Multiple doses of the *M. luteus* strain can be administered to achieve colonisation and replacement of the resident, skin disorder causing bacteria or fungi. The *M. luteus* strains may need to be administered to the patient once only or repeatedly. Repeat treatments may be once a month, once a week, once a day, two or three times a day, or as may otherwise be required. Conveniently, the administration may be effected as part of the patient's routine grooming.

For treatment of body odour the *M. luteus* or composition of the invention should be applied to affected body parts such as axilla, groin, feet and skin folds. Most conveniently application is made after showering.

Acne treatment is most commonly required on the face. Applications of *M. luteus* may be in the form of a face wash, cleanser, moisturiser or similar used in routine grooming, or may be applied in the form of a cream or the like.

Skin infections can affect a variety of surfaces and body parts including skin folds. Tinea commonly occurs on the feet (*Tinea pedis*), groin (*Tinea cruris*), body (*Tinea corporis*), toenails (*Tinea unguium*), or scalp (*Tinea capitis*) As discussed above Tinea is a polymicrobial skin infection. Athlete's foot is usefully treated by direct application of the organism or composition of the invention to the affected area. Oils and powders are particularly useful for this purpose.

Many infections also arise at sites of trauma, for example scratches, grazes and cuts. These trauma sites allow colonisation by normal commensal organisms of the skin. Common skin infectious agents treatable using *M. luteus* or compositions of the invention are listed above and include *S. pyogenes*, *S. aureus*, *P. acnes*, and aerobic coryneforms.

*Staphylococcus aureus* (including methicillin resistant strains) are commonly carried on the skin and in the nasal passages and lungs. Nasal sprays of the invention can be used to treat or eliminate the carriage of *S. aureus* and similar pathogens. Therapeutic treatment of health and food workers to eliminate resistant *S. aureus* from skin, and nasal passages is desirable to prevent spread of infection.

Mastitis involves mammary gland infection by skin bacteria. Prevention or treatment of mastitis is usefully achieved by teat or nipple washes.

To facilitate colonisation, in one embodiment the treatment method of the invention includes a preliminary step of pre-treating the individual to at least reduce the normal microflora present on the skin surface. This pre-treatment may be as simple as carrying out normal grooming procedures such as washing with soap and water, or using a salt scrub, showering, skin cleansing, and usual treatments for acne. *M. luteus* of the invention is then administered to the depopulated environment to repopulate same.

Successful colonisation of the individual's skin by the *M. luteus* strain can be established by culturing the bacteria of the individual's skin, and identifying the *M. luteus* using methods well known in the art for bacterial strain identification such as 16 sRNA identification.

The methods and uses of the invention may further comprise the use of one or more secondary antibacterial agents, as discussed above.

The *M. luteus* and compositions of the invention may also be used in conjunction with existing treatment products such as acne treatment products, deodorants and antiperspirants, cleansers, toners and moisturisers but not limited thereto.

Where the term comprise, comprises, comprised or comprising are used in this specification, they are to be interpreted as specifying the presence of the stated features, integers, steps or components referred to, but not to preclude the presence or addition of one or more other features, integers, steps, components or groups thereof.

Various aspects of the invention will now be illustrated in a non-limiting way by reference to the following experimental section.

EXAMPLES

Example 1

Isolation and Characterisation of *Micrococcus luteus* Q24

*M. luteus* strain Q24 was isolated from the skin of a healthy adult male subject and cultured into blood agar plates. The plates were incubated at 35-37° C., 5% $CO_2$ in air.

Comparison of the amplified 16S rRNA variable gene region with data bases established the organism to be *Micrococcus luteus*. Its appearance on blood agar is consistent with *Micrococcus luteus*. Individual colonies are convex, circular, entire, smooth and become creamy-yellow-pigmented on prolonged incubation. Gram-stained appearance was of Gram-positive cocci (1 micrometre diameter) in irregular clumps.

Physiological and Biochemical Characteristics of *M. luteus* Q24

The biochemical characteristics were determined using the ID32 *Staph* and API 50 CH kits (bioMérieux).

| | |
|---|---|
| Pigmentation | yellow |
| Urease | positive |
| Nitrate reduction | negative |
| Acetoin production | negative |
| Novobiocin sensitivity | sensitive |
| Esculin hydrolysis | negative |
| Casein hydrolysis | positive |
| Fermentation: | |
| Glycerol | negative |
| Erythritol | negative |
| D-Arabinose | negative |
| L-Arabinose | negative |
| D-Xylose | negative |
| Adonitol | negative |

-continued

| | | |
|---|---|---|
| α-Methyl-xyloside | negative | |
| Galactose | negative | |
| D-Glucose | negative | |
| D-Fructose | negative | |
| L-Sorbose | negative | |
| Maltose | negative | |
| Lactose | negative | |
| Trehalose | negative | |
| D-Mannose | negative | |
| Raffinose | negative | |
| Mannose | negative | |
| Mannitol | negative | |
| Ribose | negative | |
| Dulcitol | negative | |
| Inositol | negative | |
| Sorbitol | negative | |
| Saccharose | negative | |
| N-acetylglucosamine | negative | |
| D-Turanose | negative | |
| Arabinose | negative | |
| Cellobiose | negative | |
| α-Methyl-D-mannoside | negative | |
| α-Methyl-D-glucoside | negative | |
| Amygdaline | negative | |
| Salicin | negative | |
| Melibiose | negative | |
| Inulin | negative | |
| Melezitose | negative | |
| Amidon | negative | |
| Glycogen | negative | |
| Xylitol | negative | |
| β-Gentiobiose | negative | |
| D-Tagatose | negative | |
| D-Fucose | negative | |
| L-Fucose | negative | |
| D-Arabitol | negative | |
| L-Arabitol | negative | |
| Gluconate | negative | |
| 2 ceto-gluconate | negative | |
| 5 ceto-gluconate | negative | |
| β-Galactosidase | negative | |
| Arginine phosphatase | positive | |
| Pyrrolidonyl acrylamidase | negative | |
| β-Glucouronidase | negative | |
| Arginine dihydrolyase | negative | |
| Ornithine decarboxylase | negative | |

Inhibitory Activity of *Micrococcus luteus*

A. The Ability of *M. luteus* Strain Q24 to Inhibit Bacteria Associated with Skin Disorders was Assessed in a Deferred Antagonism Test Against Nine Standard Indicator Strains.

The P-typing test involves first growing the test strain on blood agar as a diametric streak culture. After removing this growth, the agar surface is sterilized with chloroform vapour, aired and the 9 standard indicator bacteria (set out in table 1) are cross-streaked across the line of the original test strain inoculum. Following incubation, interference with growth of the indicators in the vicinity of the original producer streak is taken as indicative of inhibitory activity. Relative zone size is indicated qualitatively on a scale of +− (reduction in growth on indicator in a zone approximately the width of the original producer streak) to +++ (Clear inhibition zone three times the width of the original producer streak).

The results are given below in Table 1.

TABLE 1

| Indicator designation | Strain specification | Activity |
|---|---|---|
| I1 | *Micrococcus luteus* strain T-18 | +++ |
| I2 | *S. pyogenes* (Group-A)[2] strain FF22, M-type 52, T-pattern 3/13 | ++ |
| I3 | *S. anginosus* (Group-F) strain T-29 | + |

TABLE 1-continued

| Indicator designation | Strain specification | Activity |
|---|---|---|
| I4 | *S. uberis* (Group-E) strain T-6, (ATCC 27958) | + |
| I5 | *S. pyogenes* (Group-A) strain 71-679, M-type 4, T-pattern 4 | ++ |
| I6 | *Lactococcus lactis* (subspecies *lactis*) (Group-N) strain T-21 | +++ |
| I7 | *S. pyogenes* (Group-A) strain 71-698, M-type 28, T-pattern 28 | ++ |
| I8 | *S. pyogenes* (Group-A) strain W-1,, M-type M87, T-pattern 6 | + |
| I9 | *S. equisimilis* (Group-C) strain T-148 | ++ |

[1]Tagg and Bannister "Fingerprinting" beta-haemolytic *streptococci* by their production of and sensitivity to bacteriocine-like inhibitors. *J Med Microbiol* 12, 397-411.
[2]Lancefield group designation The table 1 shows a P-type 777 pattern signifying inhibitory activity against all nine indicators. Activity was particularly strong against a *Micrococcus* strain, *S. pyogenes*, *L. lactis* and *S. equisinilis*.

By using this deferred antagonism test, the inhibitory spectrum of *M. luteus* Q24 was further assessed and the results are shown in Table 2.

TABLE 2

Activity against additional potential indicator strains

| Species | Number Tested | Sensitive to *M. luteus* Q24 |
|---|---|---|
| *Staphyococcus aureus** | 24 | 24 |
| *Staphylococcus simulans* | 1 | 1 |
| *Staphylococcus xylosus* | 1 | 1 |
| *Staphylococcus saprophyticus* | 1 | 1 |
| *Staphylococcus carnosus* | 1 | 1 |
| *Staphylococcus cohnii* | 1 | 0 |
| *Streptococcus mutans* | 9 | 0 |
| *Streptococcus dysgalactiae* | 3 | 3 |
| *Streptococcus salivarius* | 10 | 0 |
| *Streptococcus agalactiae* | 3 | 3 |
| *Corynebacterium minutissimus* | 1 | 1 |
| *Corynebacterium diphtheriae* | 1 | 1 |
| *Corynebacterium ulcerans* | 1 | 1 |
| *Lactobacillus casei* | 1 | 1 |
| *Lactobacillus acidophilus* | 1 | 1 |
| *Micrococcus lysodiekticus* | 1 | 1 |
| *Kocuria varians* (variacin producer) | 1 | 0 |
| *Enterococcus faecalis* | 3 | 1 |
| *Candida albicans* | 4 | 0 |
| *Prevotella intermedia* | 2 | 2 |
| *Porphyromonas gingivalis* | 2 | 2 |
| *Propionibacterium acnes* | 1 | 1 |
| *Propionibacterium propionicus* | 1 | 1 |
| *Pseudomonas aeruginosa* | 1 | 0 |
| *Micrococcus luteus* Q24 (Producer strain) | 1 | 0 |

*strains tested included 20 methicillin resistant strains.

Example 2

A. Topical Application to Prevent Body Odour

A saline suspension of *M. luteus* Q24 with a concentration of approximately $1 \times 10^6$ CFU per dose was inoculated by swabbing one axilla of each of several test subjects after showering.

The inoculated strain has been shown to persist for at least 24 hours. Subjective comparison of the body odour of the two axilla by the subjects and by "blinded" assessors found the Q24 inoculated axilla to be relatively odour free when compared with the control axilla.

B. Effect of *M. luetus* Q24 on Axilla Odour

Deodorant Stick Formulation

| Cocco butter | 16 g |
|---|---|
| Shea butter | 12 g |
| Potasium alum | 2.3 g |
| Q24 freeze-dried powder | 0.04 g |

The deodorant stick was prepared by melting cocco and shea butter at 40° C. *M. luteus* Q24 freeze-dried powder was mixed with the molten butter and poured into a deodorant stick container. The mixture was cooled at 4° C. until solid.

The Q24 cell count for the deodorant stick was $5 \times 10^6$ cfu/g

The subject had a shower as per usual and then applied the Q24 deodorant stick to the left axilla. The right axilla was used as a control. A cotton swab was soaked in sterile saline/1% Tween 80 and used to swab the axilla region. The swab sample was resuspended in 1 ml saline/1% Tween 80. Ten fold dilutions of the sample were spiral plated onto Blood agar plates or *Corynebacterium* isolation medium (Columbia blood agar base 22 g, Calcium carbonate 0.5 g, Lecithin 0.5 g, Tween 80 2.5 ml, Human blood agar 20 ml, sodium tellurite 10 ml, distilled water 500 ml). The plates were incubated at 37° C., 5% $CO_2$ in air. Staphlococci counts were determined from the Blood agar plates after 24 hour incubation and the corynebacterial counts on the selective media after 2 days.

Body odour was self assessed by smelling their own axilla (0—no odour, 1 slight odour, 3—strong odour, 5—very strong odour).

TABLE 3

Effect of *M. luteus* Q24 on *staphylococcus* and *corynebacterial* axilla populations.

| | Staphylococcus counts | | Corynebacterium counts | |
|---|---|---|---|---|
| Time (hours) | Left axilla | Right axilla | Left axilla | Right axilla |
| 0 | $1.6 \times 10^5$ | $3.4 \times 10^5$ | $3.8 \times 10^3$ | $4.5 \times 10^3$ |
| 7 | $8.2 \times 10^4$ | $6.4 \times 10^5$ | $9.0 \times 10^2$ | $3.5 \times 10^4$ |
| 24 | $1.0 \times 10^5$ | $4.2 \times 10^6$ | $3.3 \times 10^3$ | $8.2 \times 10^4$ |

TABLE 4

Effect of *M. luteus* on axilla odour

| Time | Odour score | |
|---|---|---|
| (hours) | Left | Right |
| 0 | 0 | 0 |
| 7 | 0 | 3 |
| 24 | 1 | 5 |

The *M. luteus* Q24 had a slight effect on the *staphylococcus* cell counts while there was a 0.6 log reduction in the corynebacterial cell counts at 7 hours (Table 3). The odour score on the control axilla increased over 24 hours while the treated axilla only slightly increased (Table 4).

These results confirm the earlier assessment that Q24 is effective in reducing body odour. This is believed to be by action against the aerobic diphtheroids commonly implicated in body odour.

Example 3

Effect of *M. luteus* Q24 on Athlete's Foot

Formulation:

| Grapeseed oil | 2.0 g |
|---|---|
| Chamomile oil | 0.06 g |
| Q24 freeze-dried powder | 0.1 g |

The oil formulation was prepared by mixing *M. luteus* freeze-dried powder with the oils to produce a suspension formulation.

The Q24 cell count for the deodorant stick was $1.2 \times 10^7$ cfu/g.

The formulation was applied to the infected area of five subjects with athlete's foot daily for three days. Within 10 minutes the itchy symptoms had disappeared. After three days no further application was required due to cessation of the signs of infection.

All references including patents and publications cited in this specification are incorporated herein by reference.

What we claimed is:

1. A biologically pure culture of *M. luteus* strain Q24 on deposit at Deutsche Sammlung von Mikroorganisms Und Zellkulturen GmbH, Braunschweig, Germany, under accession number DSM 17172.

2. A composition comprising a strain of *M. luteus* Q24 according to claim 1 effective to at least inhibit one or more bacteria selected from the group consisting of *Staphylococcus* species, *Propionibacterium* species, *Corynebacterium* species, *Streptococcus* species, and aerobic diphtheroids.

3. The composition according to claim 2, wherein the one or more bacteria is selected from the group consisting of *Propionibacterium acnes, Staphylococcus aureus, Staphylococcus saprophyticu, Staphylococcus simulans, Corynebacterium diphtheriae, Corynebacterium ulcerans, Corynebacterium minutissimum, Corynebacterium tenuis, Streptococcus pyogenes, Streptococcus agalactiae,* and *Streptococcus dysgalactiae.*

4. The composition of claim 3 wherein the *Staphylococcus aureus* is methicillin resistant.

5. The composition of claim 2, wherein the composition is formulated for topical administration.

6. The composition of claim 5 which is a wash, cream, lotion, gel, oil, emulsion, unguent, suspension, powder, aerosol spray, nasal spray, roll-on, stick, semi-solid or solid formulation.

7. The composition of claim 2, which further comprises one or more secondary antibacterial agents.

8. The composition of claim 7, wherein the secondary antibacterial agent is a bacteriocin-like inhibitory substance (BUIS).

9. The composition of claim 8 wherein the BLIS is selected from nisin, epidermin and salivaricin A, salivaricin $A_1$, salivaricin $A_2$, and salivaricin B.

10. The composition of claim 7 wherein the secondary antibacterial agent is potassium alum.

11. The composition of claim 2, which is in unit dosage form.

12. The composition of claim 11 which contains from about $10^4$ to $10^8$ CFU/g of *M. luteus* per dose.

13. The composition of claim 11 which contains from about $10^6$ to $10^7$ CFU/g of *M. luteus* per close.

* * * * *